(12) United States Patent
Fan et al.

(10) Patent No.: US 11,624,088 B2
(45) Date of Patent: Apr. 11, 2023

(54) METHODS, COMPOSITIONS, AND SYSTEMS FOR MAPPING LOCATIONS OF SINGLE MOLECULES IN MULTI-DIMENSIONAL SPACE

(71) Applicant: 13.8, Inc., Palo Alto, CA (US)

(72) Inventors: Hei Mun Christina Fan, Palo Alto, CA (US); Stephen P. A. Fodor, Palo Alto, CA (US)

(73) Assignee: 13.8, Inc., Palo Alto, CA (US)

( * ) Notice: Subject to any disclaimer, the term of this patent is extended or adjusted under 35 U.S.C. 154(b) by 0 days.

(21) Appl. No.: 17/376,396

(22) Filed: Jul. 15, 2021

(65) Prior Publication Data

US 2022/0017952 A1 Jan. 20, 2022

Related U.S. Application Data

(60) Provisional application No. 63/053,326, filed on Jul. 17, 2020.

(51) Int. Cl.
*C12Q 1/6841* (2018.01)
*G01N 33/543* (2006.01)
*G01N 33/53* (2006.01)
*C12Q 1/6804* (2018.01)

(52) U.S. Cl.
CPC ......... *C12Q 1/6841* (2013.01); *C12Q 1/6804* (2013.01); *G01N 33/5308* (2013.01); *G01N 33/54326* (2013.01); *G01N 2458/10* (2013.01); *G01N 2570/00* (2013.01)

(58) Field of Classification Search
CPC .. C12Q 1/6804; C12Q 1/6806; C12Q 1/6834; C12Q 1/6841; G01N 33/5308; G01N 33/54326; G01N 2458/10; G01N 2570/00
See application file for complete search history.

(56) References Cited

U.S. PATENT DOCUMENTS

| | | | |
|---|---|---|---|
| 9,476,101 B2 | 10/2016 | Pregibon et al. | |
| 9,727,810 B2 | 8/2017 | Fodor et al. | |
| 10,002,316 B2 | 6/2018 | Fodor et al. | |
| 10,913,975 B2 | 2/2021 | So et al. | |
| 2016/0289740 A1 | 10/2016 | Fu et al. | |

(Continued)

OTHER PUBLICATIONS

Valignet et al. (Proc. Natl. Aca. Sci., 2005, 102(12):4225-4229) (Year: 2005).*

(Continued)

*Primary Examiner* — Jeremy C Flinders
(74) *Attorney, Agent, or Firm* — Wilson Sonsini Goodrich & Rosati

(57) ABSTRACT

The invention(s) cover a composition, where units of the composition are configured to interact with each other (e.g., as neighbors) in order enable decoding of positions of captured target material relative to neighboring units of the composition. In embodiments, the composition includes: a body; and a set of molecules coupled to the body, the set of molecules comprising a first subset and a second subset, wherein the first subset is structured for target analyte capture, and wherein the second subset is structured for interactions with one or more neighboring objects. The invention(s) also cover systems incorporating one or more units of the composition and methods implementing units of the composition.

8 Claims, 9 Drawing Sheets

(56) References Cited

U.S. PATENT DOCUMENTS

2016/0312276 A1    10/2016  Fu et al.
2018/0180601 A1*   6/2018   Pedersen .......... G01N 33/56977

OTHER PUBLICATIONS

Soto et al. (J. Amer. Chem. Soc., 2002, 124:8508-8509) (Year: 2002).*
Yanyi Huang et al., Centrifugal micro-channel array droplet generation for highly parallel digital PCR, Lab on a Chip, Jan. 21, 2017, pp. 235-240, vol. 17, No. 2, Royal Society of Chemistry, London, UK.

* cited by examiner

HYBRIDIZATION AND POLYMERASE EXTENSION

STICKY END LIGATION AND POLYMERASE EXTENSION mRNA 1 @ Particles 9, 10, 17, and 23
mRNA 2 @ Particles 1, 2, 3, 8, 14, and 19
...
...
...
mRNA N @ Particles 15, 16, 17, and 21

METHODS, COMPOSITIONS, AND SYSTEMS FOR MAPPING LOCATIONS OF SINGLE MOLECULES IN MULTI-DIMENSIONAL SPACE

CROSS-REFERENCE TO RELATED APPLICATIONS

This application claims the benefit of U.S. Provisional Application No. 63/053,326 filed on 17 Jul. 2020, which is incorporated in its entirety herein by this reference.

TECHNICAL FIELD

This invention relates generally to the sample characterization field, and more specifically to new and useful systems, methods, and compositions for multidimensional target mapping in the sample characterization field.

BACKGROUND

With an increased interest in understanding distributions of particular target analytes within a biological sample, improved compositions, methods, and systems that allow for analyte mapping are becoming highly valuable. Current technologies are limited in resolution of mapping, ability to map in multiple dimensions, ability to map across scales of magnitude, ability to map different types of analytes, and/or in other manners. Furthermore, compositions for enabling mapping can require high precision and uniformity in composition in order to enable accurate mapping. Thus, there is a need in the sample characterization field for new and useful systems, methods, and compositions for multidimensional target mapping in the sample characterization field.

DESCRIPTION OF THE PREFERRED EMBODIMENTS

Figure 1A:
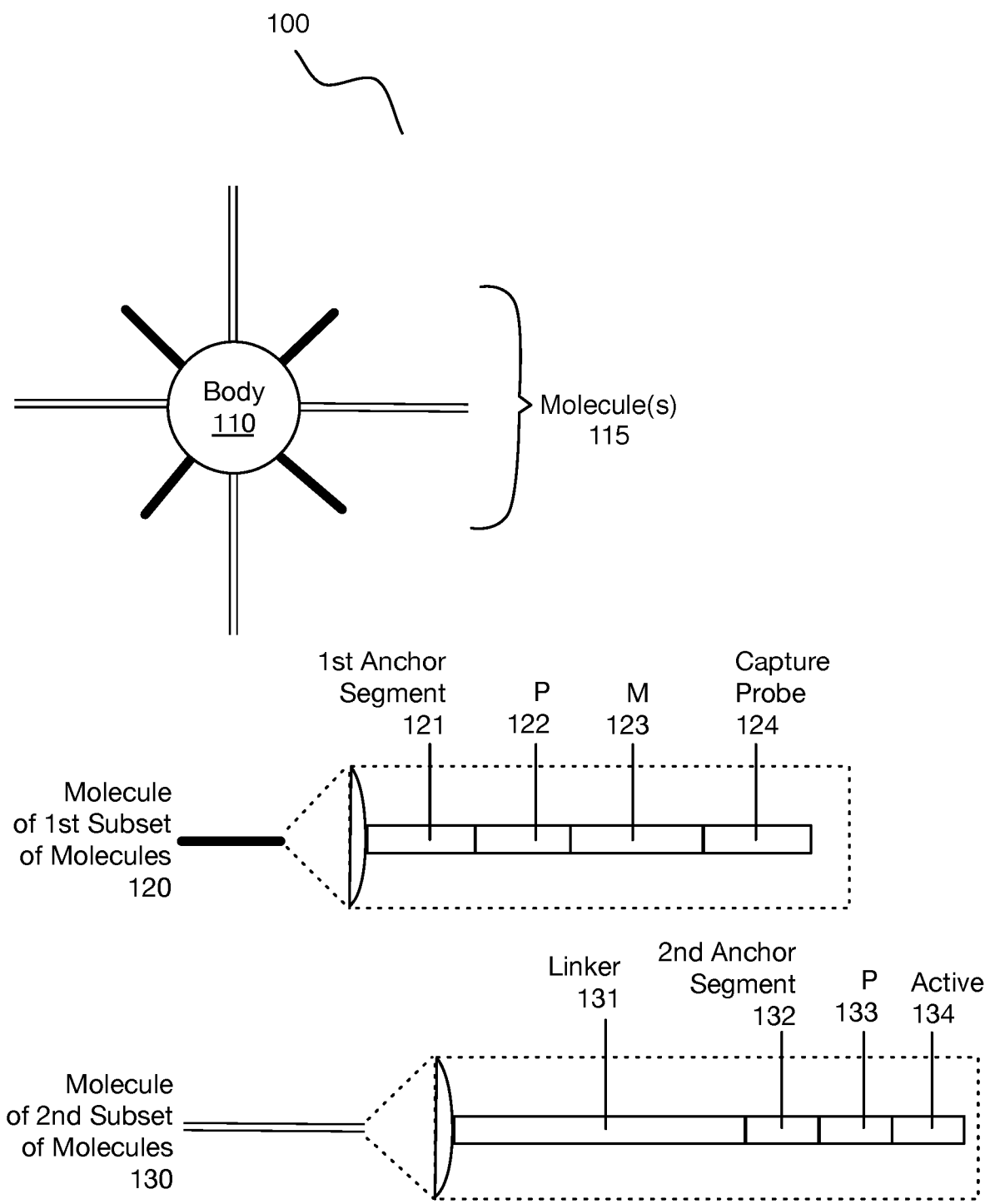
FIG. 1A depicts a schematic of an embodiment of a composition for mapping locations of targets in multidimensional space.

The following description of the preferred embodiments of the invention is not intended to limit the invention to these preferred embodiments, but rather to enable any person skilled in the art to make and use this invention.

1. BENEFITS AND APPLICATIONS

The invention(s) described can confer several benefits over conventional systems, methods, and compositions.

The invention(s) confer(s) the benefit of providing non-naturally occurring compositions for facilitating capture of target biological material from a sample and mapping distributions of target biological material in space (e.g., two-dimensional [2D] space, three-dimensional [3D] space), while providing one or more identifiers of the target biological material and/or neighboring material. Such compositions can include materials that have been modified from their natural states (e.g., in terms of providing structural differences from natural compositions). Furthermore, the invention(s) relate to combinations of materials, where the combinations of materials are non-naturally occurring (e.g., there is no naturally occurring counterpart to the compositions described and claimed).

As such, applications of the invention(s) can include improved performance of spatial multi-omics (e.g., spatial transcriptomics, spatial genomics, etc.), using novel functionalized particles for target detection and mapping.

The invention(s) also confer(s) the benefit of providing mechanisms for efficient capture and labeling of target material (e.g., DNA, RNA, miRNA, proteins, small molecules, single analytes, multianalytes, etc.) in order to enable analyses for mapping distributions of target material. For nucleic acid targets, capture probes of compositions described can include complementary molecules to the nucleic acid targets. For protein targets or small molecule targets, capture probes of the compositions described can include antibodies or aptamers conjugated with specific nucleic acid sequences for detection.

The invention(s) also confer(s) the benefit of enabling mapping of targets in multiple dimensions (e.g., 2D, 3D), where mapping can be performed in relation to whole tissue structures, tissue pieces (e.g., tissue slices as in histology, in relation to biopsied tissues, in relation to tissue blocks in relation to seeded scaffolds, etc.), droplets (e.g., of an emulsion), organs, whole organisms, cell suspensions, single cells, organelles, within organelles, viruses, microorganisms, and other natural structures. Mapping can additionally or alternatively be performed in relation to non-naturally occurring structures, such as microwells, microarrays, scaffolds, and other non-naturally occurring structures.

By incorporating molecular structures configured for interactions with neighboring objects (e.g., other units of the composition), the invention(s) enable capturing of targets, and subsequent decoding of spatial relationships between particles associated with the captured targets, which can then be used to determine locations of the targets in space (e.g., in situ, with respect to other naturally and non-naturally occurring structures, etc.)

In relation to mapping in multiple dimensions, particles of the composition(s) described can be implemented in monolayer form (e.g., with systems that apply magnetic or other forces to form particle monolayers), with sample (e.g., tissue, cells) positioned adjacent the monolayer for subsequent processing and mapping. Monolayers can be stacked between samples, in order to enable 3D mapping. Alternatively, particles of the composition(s) described can be infused into a sample/specimen (e.g., by magnetic force, by electroporation, by using vectors, etc.). Alternatively, particles of the composition(s) described can be coupled to a surface of a sample/specimen (e.g., by chemical binding, by magnetic binding, by other binding), in order to enable surface mapping. Alternatively, particles of the composition(s) described can be guided or otherwise retained in 3D structures (e.g., in grids, in non-grid structures), such as microwells, microarrays (e.g., with nucleic acids capturing particles), scaffolds, or other 3D structures.

In a related application, physical or other forces can be used to define structures (e.g., close packed structures) for distributions of particles that interact with samples to enable mapping.

Alternatively, in relation to mapping in multiple dimensions, particles of the composition(s) described can be randomly distributed in space.

The invention(s) also confer(s) the benefit of enabling applications in spatial transcriptomics. For instance, compositions, methods, and systems described can be used for mapping of targets in a sample over time, in order to understand disease pathology and progression (e.g., spread of targets and changes in expression over time).

Additionally or alternatively, the invention(s) can confer any other suitable benefit.

2. PARTICLE COMPOSITION

As shown in FIG. 1A, an embodiment of a composition 100 for mapping of molecules includes: a body 110 and a set of molecules 115 coupled to the body 110 and structured for functionalization of the composition 100.

In embodiments, the set of molecules 115 can include a first subset of molecules 120 structured for target analyte capture, where a unit of the first subset 120 can include one or more of: a first anchor segment 121, a first particle identification segment (P) 122, a unique molecule identifier (M) 123, and a capture probe 124. In embodiments, the set of molecules 115 can include a second subset of molecules 130 structured for interactions with one or more neighboring objects (e.g., other units of the composition 100), where a unit of the second subset 130 can include one or more of: a linker region 131, a second anchor segment 132, a second particle identification segment (P) 133, and an active segment 134 for interactions with a neighboring object. In applications, the composition 100 can be provided as a set of particles (e.g., in solution), wherein each of the set of particles is coupled to (e.g., coated with) molecules for various assays associated with mapping of locations of target molecules of a biological sample.

The composition 100 can be configured for processes and reactions associated with target capture and neighboring object detection, including one or more of: reverse transcription reactions (RT-reactions) for cDNA synthesis associated with target capture, amplification reactions (e.g., PCR) for amplification of cDNA, high throughput sequencing, ligation, hybridization, polymerase extension, and other suitable reactions. Such reactions can be performed in relation to systems (described in further detail below) including one or more of: natural structures (e.g., organelles, cells, tissues, organs, natural scaffolds, etc.), synthetic structures (e.g., arrays, synthetic scaffolds, microwells, etc.), and/or random dispersions of sample materials.

In some non-limiting examples, sample material from which targets can be captured can include one or more of: nervous system biological material, cardiovascular system biological material, integumentary system biological material, skeletal system biological material, muscular system biological material, respiratory system biological material, digestive system biological material, endocrine system biological material, urinary system biological material, and reproductive system biological material. Cellular material can be associated with normal and diseased states, including one or more of: cancer cells, circulating tumor cells, metastatic cells, benign cells, or any combination thereof. In embodiments, the sample can include solid/contiguous tissue material obtained from a subject.

Additional aspects of the invention(s) and applications of use are described in more detail below.

2.1 Particle

The body 110 functions to provide a substrate to which the set of molecules 115 can be coupled to, in order to provide functionalization for the composition 100 with respect to implementation of respective assays and reactions, and subsequent mapping operations.

Figure 1B:
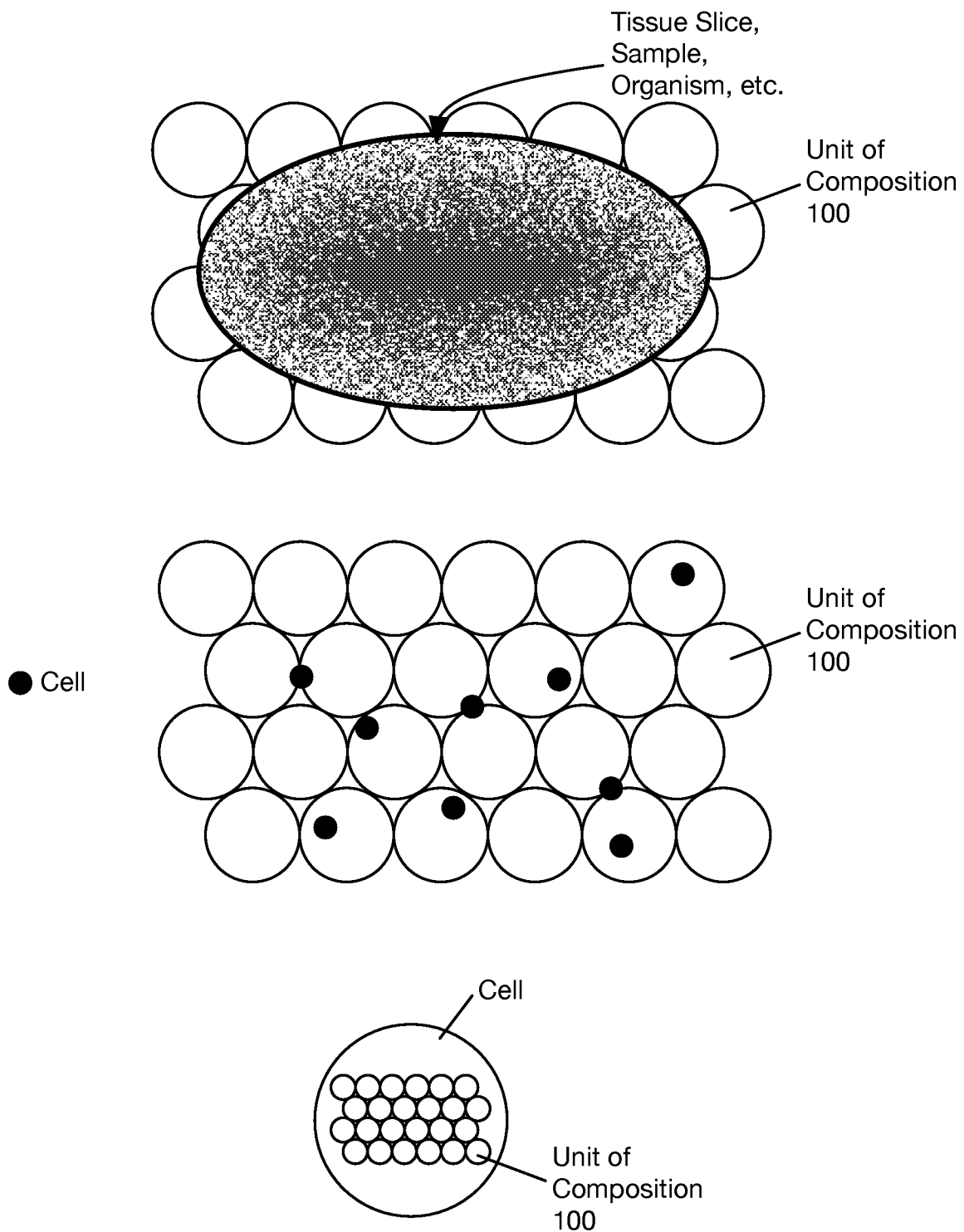
FIG. 1B depicts various scales and sample types for which units of the composition can be used.

In relation to morphology, the body 110 can have the form of a microsphere. Alternatively, the body 110 can have the form of a non-spherical (e.g., ellipsoidal, prismatic, polyhedral, amorphous, etc.) body, where a cross section taken through the body 110 is non-circular. However, the body 110 can alternatively have another suitable form. In relation to dimensions, the body 110 can have a diameter (or characteristic width) on the order of nanometers to micrometers in dimension, where particle size determines the resolution of mapping. Examples of particle scales are shown in FIG. 1B, in relation to mapping of targets relative to cells, tissues, and organs, as well as mapping of targets located within a cell or other component. Nanometer-scale applications of the body 110 can be associated with intracellular, sub-cellular scale, or other nanometer-scale mapping applications. Micrometer-scale applications of the body 110 can be associated with intercellular, tissue-scale, cellular scale, or other micrometer-scale mapping applications. The body 110 can alternatively have other suitable characteristic dimensions. During use, a solution of the particles can have uniform (or approximately uniform) particle sizes; alternatively, during use, a solution of the particles can have non-uniform particle sizes. In a first example for examining target distributions in a 10 mm×10 mm tissue slide in 2D, the body 110 and coupled molecules can provide a characteristic particle dimension of 10 um in diameter, thereby requiring approximately 1000×1000=1 million unique particles for target mapping relative to the tissue slice.

In relation to density, the body 110 can be configured to have a density greater than the density of process liquids intended for use with the composition 100 (e.g., in relation to specific reactions or assays), such that the composition 100 settles within the process liquid(s) by gravity during operation. Alternatively, the body 110 can be configured to have a density equal to the density of process liquids intended for use with the composition 100 (e.g., in relation to specific reactions or assays), such that the composition 100 sits in equilibrium within the process liquid(s) during operation. Still alternatively, the body no can be configured to have a density less than the density of process liquids intended for use with the composition 100 (e.g., in relation to specific reactions or assays), such that the composition 100 is buoyant within the process liquid(s) during operation. For instance, buoyant particles can be distributed in a film across a surface of a process fluid, and a sample can be positioned adjacent to the buoyant particles in order to enable target mapping.

In relation to thermal properties, the body no is configured to operate between a lower temperature limit (e.g., associated with low temperature reactions and processes, associated with storage, etc.) and an upper temperature limit (e.g., associated with high temperature reactions and processes, such as for thermocycling). However, the body 110 can be configured for other operating temperatures.

In relation to physical properties, the body no is configured to maintain structure in solution (e.g., in buffer during storage, in solution during performance of an assay). As such, the body no is configured to be non-swelling and non-leaching. However, in alternative embodiments, the body 110 can be configured to swell a desired amount (e.g., in relation to achieving a desired size or morphology for processing or use in an application), configured to leach certain compounds (e.g., process reagents) for performance of an assay, and/or to dissolve in a desired manner during performance of an assay or other process. Further in relation to physical properties, the body 110 can be configured with a desired degree of hydrophilicity (e.g., on a spectrum from hydrophilic to hydrophobic) in relation to performance of an assay or other process. Variations of the body no can thus have a suitable type of crosslinking (e.g., chemical crosslinking, physical crosslinking, etc.) and percentage of crosslinking (e.g., from 30-99% crosslinking), to provide a desired level of stability or degradability in conditions of use.

In relation to other surface properties, the body 110 can be configured with a desired density of binding sites, in order to enable achievement of a suitable linker/anchor density (e.g., by providing points of attachment on the body 110), where additions to the body 110 are described in more detail in sections related to molecule design below. Furthermore, the body 110 can include surface groups (e.g., hydroxyl groups, amine groups, carboxyl groups, sulfide groups, silanol groups, etc.) for coupling of linker molecules described sections below.

In relation to magnetic properties, the body no can be configured to respond to magnetic fields (e.g., in relation to assays involving retention of particles in position for subsequent mapping of target analytes from a sample). Certain regions (e.g., a core region) of the body 110 can be magnetic (e.g., magnetic, paramagnetic, etc.), and certain regions (e.g., a shell region) of the body 110 can be non-magnetic in variations of the body no. In relation to surface properties, the body 110 can be configured with or without charge, in order to facilitate binding to target material of a sample, or to facilitate fabrication involving molecules with functionality, in relation to electroporation applications.

In relation to optical properties, the body 110 can be configured to be non-fluorescent (e.g., so as to not interfere with optical-based detection assays). However, in variations, the body 110 can be configured to be optically detectable (e.g., via a non-fluorescent modality, via a fluorescent modality, via an infrared detection modality, via a thermal detection modality, etc.), for instance, for tracking purposes. Additionally or alternatively, the body no can be characterized by optical features encoding nucleic acid bases identifiable upon detection of the optical features.

In relation to mechanical properties, the body no can be configured to have a desired hardness (e.g., measured on the Mohs scale, measured on another hardness scale), in order to retain a desired level of hardness during applications of use. Additionally or alternatively, the body no can be configured with desired mechanical properties associated with one or more of: rigidity, elastic behavior (e.g., in terms of moduli, in terms of plastic and elastic deformation, etc.), viscoelastic behavior, fatigue resistance, fracture resistance, shear strength, compressive strength, tensile strength, rheological behavior (e.g., under conditions of wear), and other mechanical properties.

In relation to composition, the body 110 can be composed of one or more of: polymers (e.g. polystyrene, polystyrene-divinylbenzene, polymethylmethacrylate (PMMA), etc.), hydrogels, silica, silicon, non-porous glass, porous glass, coated glass, agarose, acrylamide, polyacrylamide, iron, steel, or ceramic materials and/or a combination of one or more suitable materials. As noted above and below, different regions of the body 110 can be composed of different materials (e.g., a core region can be composed of a first material and a shell region can be composed of a second material). In some embodiments there may be multiple regions either as multiple shell regions, or in other configurations such as amorphous or ordered spatial arrangements. In still further examples, the body 110 can include or take the form of a polymeric/molecular body (e.g., DNA nanoball, dendrimer, etc.), where, in applications, the dendrimers can be reduced in size to a "functional monomer" (i.e., as a smallest functional molecular assembly unit).

Units of the body no/functionalized particles can be preassembled into films or onto surfaces, where the films and surfaces can be configured to interact with tissues or other biological samples according to methods described in more detail below. For instance, such films with pre-assembled functionalized particles can be deposited onto a sample (e.g., tissue sample), or the sample (e.g., tissue sample) can be deposited onto a surface functionalized with units of the particles described.

2.2 First Subset of Molecules—Target Capture

As shown in FIG. 1A, the composition 100 includes a first subset of molecules 120 coupled to the body 110 and configured for target analyte capture, where a unit of the first subset 120 can include one or more of: a first anchor segment 121, a first particle identification segment (P) 122, a unique molecule identifier (M) 123, and a capture probe 124. The first subset of molecules 120 functions to provide desired chemistries (e.g., binding chemistries) for capture of targets from a sample being processed, in a manner that allows for subsequent processing and unique identification of the captured target material (e.g., using high throughput sequencing techniques). Molecules of the first subset of molecules 120 can be nucleic acid-based, with natural and/or modified nucleotides.

As shown in FIG. 1A, a unit of the first subset of molecules 120 can include a first anchor segment 121 configured for performance of a PCR-associated reaction (e.g., amplification) in downstream processing steps (e.g., post-target binding and/or synthesis of complementary molecules, such as cDNA for mRNA binding). The anchor segment 121 can thus include a PCR primer. As indicated above in relation to different types of nucleic acid-associated reactions, protein-associated reactions, and/or other reactions, the PCR primer(s) used for different units of the first subset of molecules 120 can be identical or different from each other. For instance, in a first variation, a first subset of units of the first subset of molecules 120 can include a first sequence associated with a first reaction or process, and a second subset of units of the first subset of molecules 120 can include a second sequence associated with a second reaction or process.

In embodiments, the first anchor segments 121 are coupled directly to the body 110. However, in other variations, the first anchor segments 121 can be coupled relative to other portions of the composition in another manner. For instance, the first anchor segments 121 can be coupled to a linker molecule, which couples the first anchor segments 121 to the body. The linker molecule can be configured to control density and spacing of the first subset of molecules 120 coupled to the body 110, in a manner that provides a sufficient number of sites for target capture to occur. Use of linkers can also function to prevent molecules at the surfaces of the body no from folding or otherwise forming undesired structures (e.g., secondary structures, tertiary structures, etc.). As such, in variations, the linker can be configured as a linear molecule segment, or alternatively as a branched molecule segment (e.g., dendrimer segment, other branched segment). Additionally or alternatively, linker molecules can be configured for selectable attachment (e.g., with functional groups specific to specific chemistries) and/or activatable cleavage (e.g., as in molecular scissors), to enable controlled release of material derived from captured targets from the body 110. In variations, activatable cleavage can be achieved with linkers configured to be cleave in response to one or more of: a thermal cleavage mechanism, a pH shift, a photocleaving mechanism, an enzymatic cleaving mechanism, or another suitable cleaving mechanism.

In embodiments, the first anchor segments 121 can have from 5-50 bases and can include custom primers (e.g., designed for specific targets) or non-custom primers; however, in alternative variations the first anchor segments 121 can have other suitable numbers of bases.

As shown in FIG. 1A, the first subset of molecules 120 can include a first particle identification segment (P) 122 coupled to the first anchor segment 121, which functions to provide a label that identifies the unique particle to which the molecule is coupled. The first particle identification segment (P) 122 is configured to be unique to each particle. Furthermore, the first particle identification segment (P) 122 is configured to have diversity such that each particle in a solution of particles can be uniquely identified (e.g., based on Poisson statistics). Alternatively, the first particle identification segment (P) 122 can be characterized in terms of diversity in another suitable manner. For instance, the first particle identification segment (P) 122 can be characterized by a "distance" metric, such as Hamming distance (e.g., number of mutations required to make different nucleic acid molecules identical).

In embodiments, the first particle identification segment (P) 122 can have from 5-50 bases in order to provide a sufficient number of unique sequences for a desired number of particles in solution for a given process (i.e., such that each particle can be uniquely identified, and hybridization of the particle identification segment with a target generates derivative material that can be used to associate the sequenced target with the respective particle); however, in alternative variations, the first particle identification segment (P) 122 can have other suitable numbers of bases (e.g., less than 5 bases, more than 35 bases). Additionally or alternatively, the first particle identification segment (P) 122 can have a number of bases designed to occupy a percentage of the length of a unit of the first subset of molecules 120 (e.g., 10%, 20%, 30%, etc.).

The first particle identification segment (P) can be coupled to the first anchor segment 121 or otherwise positioned along a respective molecule.

As shown in FIG. 1A, the first subset of molecules 120 can also include a unique molecule identifier (M) 123, which functions to provide a label that identifies the unique molecule (e.g., nucleic acid molecule, oligonucleotide-conjugated material, etc.) captured by the capture probe 124 during use of the composition (e.g., with respect to next generation sequencing, with respect to library preparation, etc.). The unique molecule identifier (M) 123 is configured to have diversity such that the target molecules in its vicinity can be uniquely labeled (e.g., based on Poisson statistics). Alternatively, the unique molecule identifier (M) 123 can be characterized in terms of diversity in another suitable manner. For instance, the unique molecule identifier (M) 123 can be characterized by a "distance" metric, such as Hamming distance (e.g., number of mutations required to make different nucleic acid molecules identical).

The unique molecule identifier (M) 123 can be specific to various sequencing platforms (e.g., next generation sequencing platforms). Furthermore, each of the first subset of molecules 120 can have a single unique molecule identifier (M) 123 or multiple unique molecule identifier (M) 123 segments (e.g., to provide further diversity). The unique molecule identifier (M) 123 can be configured to not end in bases (e.g., GG) (or other sequences that are less suitable for specific sequencing platforms); however, the unique molecule identifier (M) 123 segments can be configured in another suitable manner. Sequences of the unique molecule identifier (M) 123 across all molecules coupled to a particular body 110 can be configured through manufacturing to have a high degree of consistency (e.g., in relation to minimizing unintentional deletions, substitutions or additions) in order to produce low error rates during use.

Furthermore, in relation to the first particle identification segment (P) 122, the diversities of sequences of the unique molecule identifier (M) 123 and the first particle identification segment (P) 122 can be achieved by manufacture of a set random sequences, or alternatively, by a set of predetermined sequences. During manufacturing, the diversity of sequences can be achieved by chemical synthesis onto the body 110 and/or initial segments of molecules coupled to the body 110, by split-pool synthesis, by emulsion PCR (emPCR), or by other synthesis methods.

In embodiments, the unique molecule identifier (M) 123 can have from 5-50 bases total in order to provide a sufficient number of unique sequences for a desired number of target molecules intended for capture (i.e., such that each target can be uniquely identified); however, in alternative variations, the unique molecule identifier (M) 123 can have other suitable numbers of bases. Additionally or alternatively, the unique molecule identifier (M) 123 can have a number of bases designed to occupy a percentage of the length of a unit of the first subset of molecules 120 (e.g., 10%, 20%, 30%, etc.).

The unique molecule identifier (M) 123 can be directly coupled to the first particle identification segment (P) 122 or can be alternatively configured in relation to position along a molecule of the first subset of molecules 120.

Figure 2A:
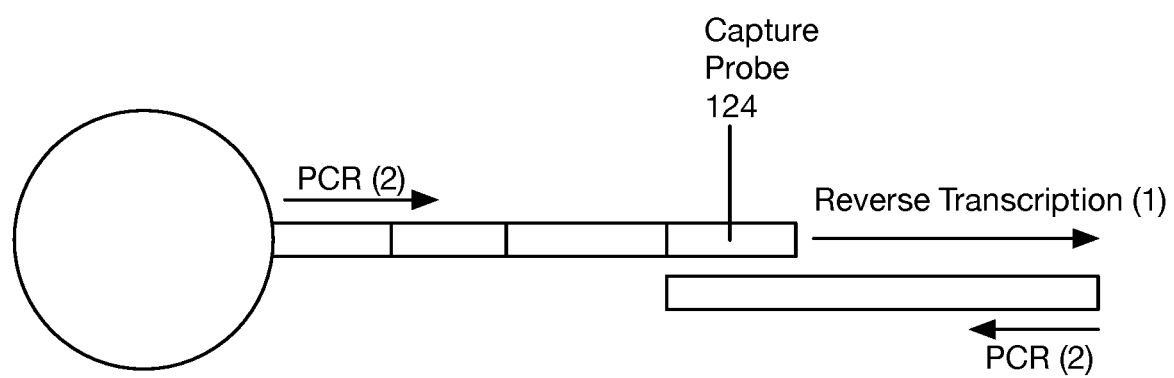
FIG. 2A depicts an embodiment of implementation of a capture probe of the composition.

As shown in FIGS. 1A and 2A, the first subset of molecules 120 can include a capture probe 124, which functions to capture target material from the sample. The capture probe 124 can be directly coupled to the unique molecule identifier (M) 123 or can alternatively configured in relation to position along a molecule of the first subset of molecules 120. In variations, analytes captured by the capture probe 124 can include: nucleic acids (e.g., DNA, mRNA, miRNA etc.) and/or oligonucleotides attached to other types of molecules (e.g., antibodies, proteins, peptides, chemicals, etc.).

In one variation, as shown in FIG. 2A, the capture probe 124 can be configured for target mRNA binding (e.g., dT, dTVN for capturing polyA mRNAs), followed by reverse transcription to append the capture probe portions of the first subset of molecules 120 with cDNA (e.g., as shown in FIG. 2A). Then, after amplification of the synthesized cDNA, high throughput sequencing can be used to read out the target molecules captured using the first subset of molecules 120. In alternative variations, inclusion of other capture probe types in the first subset of molecules 120 can configure the first subset of molecules 120 for capture of one or more of: DNA, other RNA (e.g., miRNA), proteins (e.g., antibodies, using TotalSeq™ molecules), small molecules, single analytes, multianalytes, etc.), and/or other target material. For nucleic acid targets, capture probes 124 of the first subset of molecules 120 can include complementary molecules to the nucleic acid targets. For protein targets or small molecule targets, capture probes 124 of the compositions described can include nucleic acids, where targets of a sample (e.g., proteins, peptides, antibodies, small molecules, etc.) are tagged with an oligonucleotide having a sequence complementary to that of the capture probes 124.

Units of the composition can be configured with a sufficient number of capture probes 142 (e.g., total number per particle, total number bound to particles in solution) for efficient capture of target material (e.g., ~tens of thousands of mRNA molecules per cell, another number of targets per sample type). In variations, the number of capture probes 142 utilized in solution can be 10-100× (e.g., in terms of molarity, in terms of another concentration unit, etc.) the number of targets intended for capture.

In variations, units of the first subset of molecules 120 can omit or include additional segments as needed. For instance, one or more of the first subset of molecules 120 can include segments configured to simplify library preparation steps or sequencing processes of specific sequencing platforms. In more detail, molecules of the first subset of molecules 120 can include adapter segments (e.g., associated with P5/P7 adapters for Illumina™ platforms), index sequences associated with adapters, and/or other sequences. Additionally or alternatively, additional segments can be added during sample processing (e.g., during reverse transcription, etc.). Units of the first subset of molecules 120 can additionally or alternatively include other sequences (e.g., for other fragmentation/sequencing/processing platforms).

2.3 Second Subset of Molecules—Neighboring Object Detection

As shown in FIG. 1A, the composition 100 also includes a second subset of molecules 130 coupled to the body 110 and structured for interactions with one or more neighboring objects (e.g., other units of the composition 100), where a unit of the second subset 130 can include one or more of: a linker region 131, a second anchor segment 132, a second particle identification segment (P) 133, and an active segment 134 for interactions with a neighboring object. The second subset of molecules 130 functions to provide desired chemistries for identification of neighboring objects (e.g., neighboring particles), in order to extract 2D and/or 3D mappings of sample targets during use of the composition. Molecules of the second subset of molecules 130 can be nucleic acid-based, with natural and/or modified nucleotides. Molecules of the second subset of molecules 130 can be randomly interspersed with molecules of the first subset of molecules 120 about the body 110, or can alternatively be non-randomly distributed about the body 110 relative to molecules of the first subset of molecules 120.

As shown in FIG. 1A, the second subset of molecules 130 can include a linker region 131, which functions to extend units of the second subset of molecules 130 out into space (e.g., such that units of the second subset extend beyond terminal portions of units of the first subset of molecules 120), thereby enabling interactions of the second subset of molecules 130 with neighboring objects (e.g., active segments of other particles of the composition).

In relation to composition, the linker region 131 is preferably composed of a polymer (e.g., non-nucleic acid polymer), and in a specific example, the linker region 131 can be composed of polyethylene glycol (PEG) or another suitable polymer. However, the linker region 131 can be composed of another suitable material (e.g., natural material, synthetic material).

In relation to structure, the linker region 131 can have a linear structure that extends units of the second subset of molecules 130 into space, thereby enabling interactions with neighboring objects (e.g., other units of the composition). Alternatively, the linker region 131 can have a branched or otherwise non-linear structure (e.g., dendrimer segment, other branched segment). For instance, in variations in which the linker region 131 is configured to control spacing/density of molecules coupled to the body 110, the linker region 131 can have a branched structure that reduces density and/or controls spacing/orientation of molecules coupled to the body 110. Additionally or alternatively, the linker region 131 can be configured for selectable attachment (e.g., with functional groups specific to specific chemistries) and/or activatable cleavage (e.g., as in molecular scissors), to enable controlled release of material derived from captured targets from the body 110. In variations, activatable cleavage can be achieved with linker regions configured to be cleave in response to one or more of: a thermal cleavage mechanism, a pH shift, a photocleaving mechanism, an enzymatic cleaving mechanism, or another suitable cleaving mechanism.

In relation to properties, the linker region 131 can be configured with a desired charge and/or other characteristic (e.g., level of hydrophilicity, level of hydrophobicity, etc.) that prevents undesired interactions between molecules (e.g., tangling, clumping, undesired structures, etc.). As such, the linker region 131 can be configured to extend molecules 131 into space (e.g., perpendicular from a surface of the body 110); however, the linker region 131 can be configured to extend from the body no in another suitable manner.

The linker region 131 can contribute to an overall length of units of the second subset of molecules 130, such that the persistence length between particles of the composition is overlapping (e.g., to allow interactions between neighbors). In more detail, the linker region of a first unit of the composition and the linker region of a second unit of the composition contribute to or are otherwise characterized by an overlapping persistence length between the first unit and the second unit of the composition. In variations, the linker region 131 can have a length from 0.1-5 times a characteristic dimension (e.g., diameter, width) of the body 110; however, the linker region 131 can additionally or alternatively have another suitable length (e.g., length dependent upon the overall length of molecules of the first subset 120 and the second subset 130 of molecules).

As shown in FIG. 1A, the second subset of molecules 130 can include a second anchor segment 132, configured for performance of a PCR-associated reaction (e.g., amplification of connections of nearest neighboring particles, to enable downstream mapping analyses). The second anchor segment 131 can thus include a PCR primer. In embodiments, the second anchor segments 131 are coupled to the body 110 by way of the linker region 131. However, in other variations, the second anchor segments 131 can be coupled relative to other portions of the composition in another manner. In embodiments, the second anchor segments 131 can have from 5-40 bases and can include custom or non-custom primers; however, in alternative variations the second anchor segments 131 can have other suitable numbers of bases.

As shown in FIG. 1A, the second subset of molecules 130 can include a second particle identification segment (P) 133, coupled to the second anchor segment, which functions to provide a label that identifies the unique particle to which the molecule is coupled. The second particle identification segment (P) 132 is configured to be unique to each particle. Furthermore, the second particle identification segment (P) 132 is configured to have diversity such that each particle in a solution of particles can be uniquely identified (e.g., based on Poisson statistics). Alternatively, the first particle identification segment (P) 122 can be characterized in terms of diversity in another suitable manner. For instance, the first particle identification segment (P) 122 can be characterized by a "distance" metric, such as Hamming distance (e.g., number of mutations required to make different nucleic acid molecules identical).

The second particle identification segment (P) 132 can be identical (e.g., in sequence) to the first particle identification segment (P) 122 of the first subset of molecules 120 for target capture (e.g., to facilitate efficiency of synthesis of particle identification segments), or can alternatively be non-identical to the first particle identification segment (P) 122 of the first subset of molecules 120.

In embodiments, the second particle identification segment (P) 132 can have from 5-50 bases in order to provide a sufficient number of unique sequences for a desired number of particles in solution for a given process (i.e., such that each particle can be uniquely identified, and hybridization of the particle identification segment with a target generates derivative material that can be used to associate the sequenced target with the respective particle); however, in alternative variations, the second particle identification segment (P) 132 can have other suitable numbers of bases (e.g., less than 5 bases, more than 35 bases). Additionally or alternatively, the second particle identification segment (P) 132 can have a number of bases designed to occupy a percentage of the length of a unit of the second subset of molecules 130 (e.g., 10%, 20%, 30%, etc.).

Figure 2B:
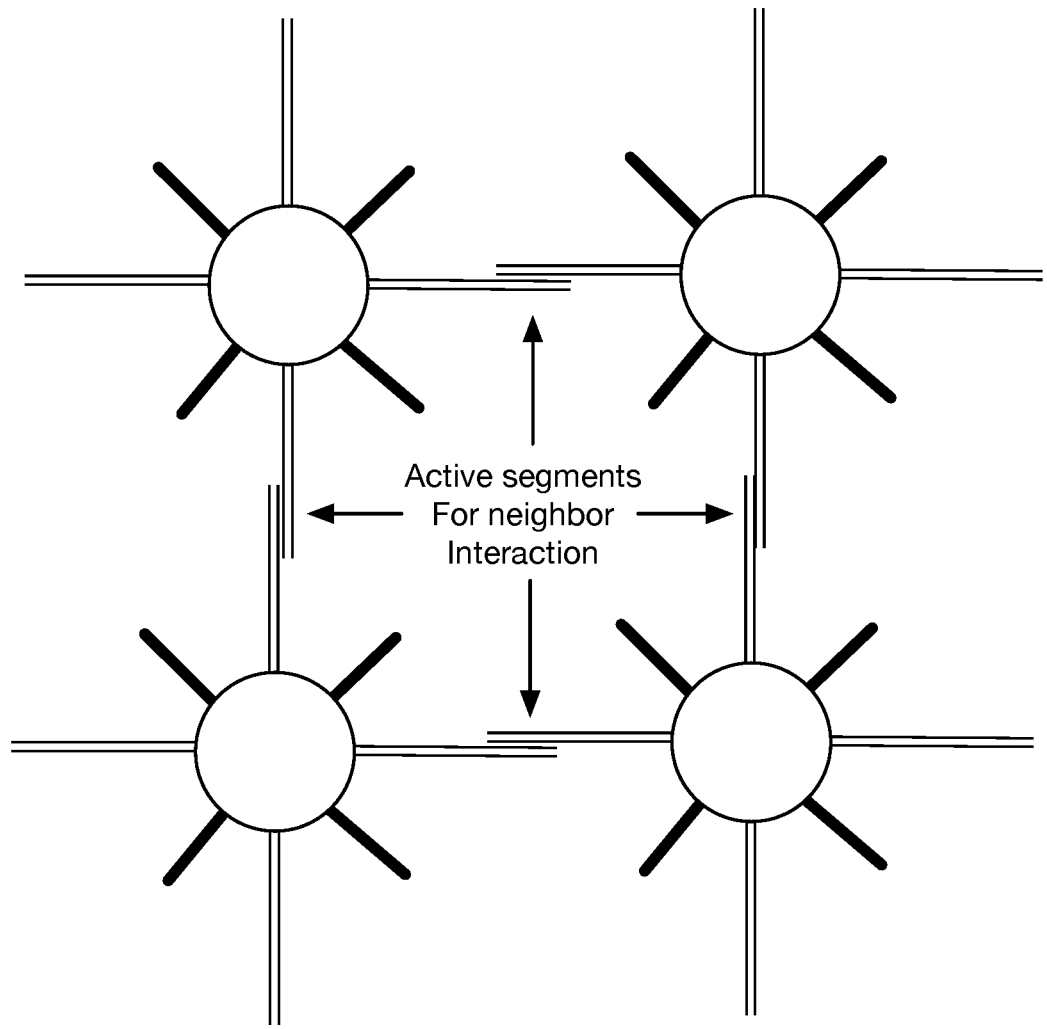
FIG. 2B depicts an embodiment of interactions between active segments of neighboring particles of the composition.

As shown in FIGS. 1A and 2B, the second subset of molecules 130 can include an active segment 134 for interactions with a neighboring object, which functions to interact with a corresponding segment of a molecule from another particle, thereby enabling determination of the particle's nearest neighbor. The active segment 134 is preferably positioned at the terminal end of each molecule of the second subset of molecules 130, in order to better promote interactions between active segments 134 of neighboring particles/objects. However, the active segment 134 can be otherwise positioned along the length of a molecule of the second subset of molecules 130.

Figure 3A:
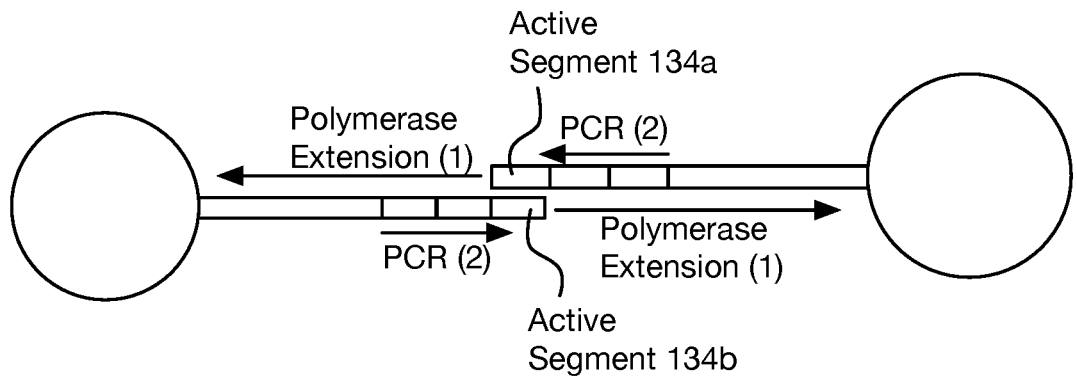
FIGS. 3A-3C depict variations of mechanisms by which active segments for neighbor identification can operate.
Figure 3B:
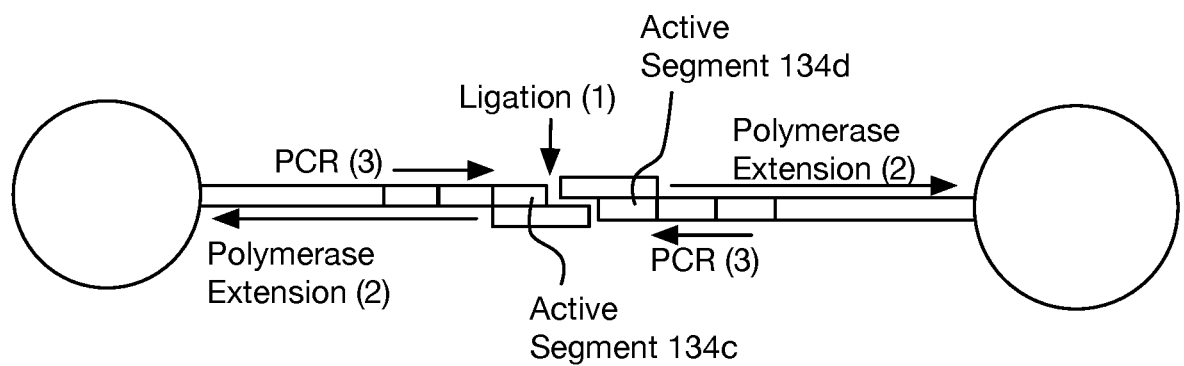
Figure 3C:
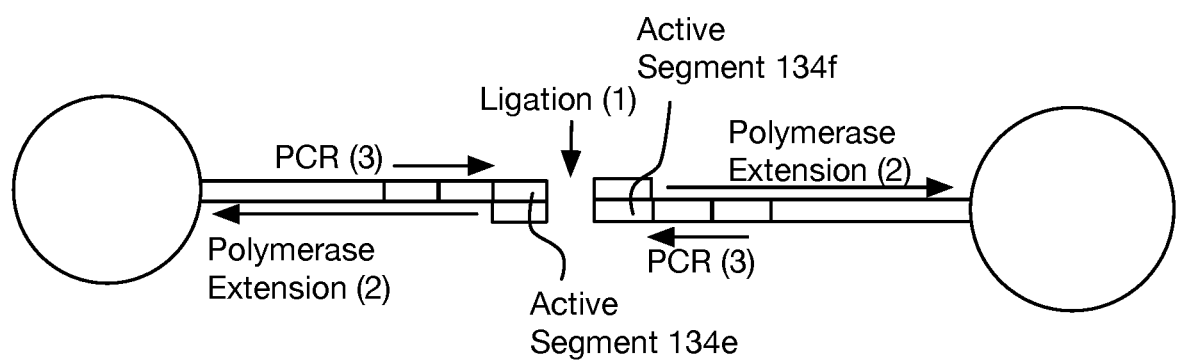

In variations, examples of which are shown in FIGS. 3A-3C, the active segment 134 can be configured to interact with corresponding interacting elements (IEs). Furthermore, the active segment 134 is configured in a manner that prevents self-hybridization or self-interaction, to prevent generation of undesired structures and/or interactions that do not involve neighboring particles. Furthermore, all active segments 134 of a respective particle are preferably configured to not interact with the other active segments of the respective particle (or preferentially interact with active segments of other particles), in order to promote efficient decoding of interactions between and positions of neighboring particles. In a specific example, a first subset of functionalized particles can have a first active segment and a second subset of functionalized particles can have a second active segment, wherein the first active segment is structured (e.g., via sequence design) to interact with the second active segment, the first active segment is structured (e.g., via sequence design) to prevent interactions with itself or other particles having the first active segment, and the second active segment is structured (e.g., via sequence design) to prevent interactions with itself or other particles having the second active segment. As such, the different active segments can be configured to interact with neighbors but not with each other. Extending the example, the set of functionalized particles can have a third active segment, a fourth active segment, etc., where with two active segments ~50% of neighboring particle interactions will generate spatial mapping reads. As the number of different active segments corresponding to different subsets of functionalized particles increases, the probability of functional interactions between neighboring functionalized particles decreases.

In a first example, as shown in FIG. 3A (described in more detail below), the active segment 134 can be configured to interact with corresponding interacting elements (IEs) by way of hybridization of complementary sequences (e.g., with a first active sequence associated with a first particle and a second active sequence of a second particle, the first and the second sequences complementary to each other), followed by polymerase extension.

In a second example, as shown in FIG. 3B (described in more detail below), the active segment 134 can be configured to interact with corresponding interacting elements (IEs) by way of implementing sticky end ligation, (e.g., with a first sticky end associated with a first particle and a second sticky end of a second particle), followed by polymerase extension.

In a third example, as shown in FIG. 3C (described in more detail below), the active segment 134 can be configured to interact with corresponding interacting elements (IEs) by way of implementing blunt end ligation, (e.g., with a first blunt end associated with a first particle and a second blunt end of a second particle), followed by polymerase extension.

However, the active segments 134 can operate by another suitable mechanism. As such, ends of the active segment 134 can be generated with or without suitable restriction enzymes, in order to provide ends that interact with neighboring particles with or without base pairing of ends. In one such variation, corresponding active segments 134 can be generated using plasmids having suitable restriction sites for generating segments having complementary ends, where the segments are coupled to the ends of synthesized units of the second subsets of molecules 130 (e.g., after the second particle identification segments 133). However, the active segments can additionally or alternatively be synthesized with units of the second subsets of molecules 130 in another suitable manner.

An example of interaction using hybridization and polymerase extension is shown in FIG. 3A, where an active segment 134a of a first particle is complementary to an active segment 134b of a second particle neighboring the first particle, and polymerase extension is performed in a first operation to link the active segments 134a and 134b. Then, PCR is used to amplify the connections of the neighboring particles in a second operation, and high throughput sequencing is used for readout of the connections of neighboring particles to extract information for mapping target distributions.

An example of interaction using sticky ends followed by ligation is shown in FIG. 3B, where an active segment 134c of a first particle is complementary to an active segment 134d of a second particle neighboring the first particle, and ligation of the sticky end in a first operation, followed by polymerase extension in a second operation, is performed to link the active segments 134c and 134d. Then, PCR is used to amplify the connections of the neighboring particles in a third operation, and high throughput sequencing is used for readout of the connections of neighboring particles to extract information for mapping target distributions.

An example of interaction using blunt ends followed by ligation is shown in FIG. 3C, where an active segment 134e of a first particle is complementary to an active segment 134f of a second particle neighboring the first particle, and ligation of the blunt end in a first operation, followed by polymerase extension in a second operation, is performed to link the active segments 134e and 134f. Then, PCR is used to amplify the connections of the neighboring particles in a third operation, and high throughput sequencing is used for readout of the connections of neighboring particles to extract information for mapping target distributions.

In variations, units of the first subset of molecules 120 can omit or include additional segments as needed. For instance, one or more of the second subset of molecules 130 can include segments configured for sequencing processes of specific sequencing platforms. In more detail, molecules of the second subset of molecules 130 can include adapter segments (e.g., associated with P5/P7 adapters for Illumina™ platforms), index sequences associated with adapters, and/or other sequences. Additionally or alternatively, additional segments can be added during sample processing (e.g., during ligation, during extension, etc.). Units of the second subset of molecules 130 can additionally or alternatively include other sequences (e.g., for other processing platforms).

In variations, the second subset of molecules 130 and/or respective active segments 134 can be configured to be releasable from the body no. For instance, the second subset of molecules 130 and/or respective active segments can be releasable from the body 110 prior to (e.g., immediately prior to) interactions with corresponding active segments from neighboring functionalized particles. Additionally or alternatively, the second subset of molecules 130 and/or respective active segments can be releasable from the body 110 after interactions with corresponding active segments from neighboring functionalized particles. Attachment and release in a controlled manner can be achieved with selective attachment mechanisms (e.g., with functional groups specific to specific chemistries) and/or activatable cleavage (e.g., as in molecular scissors, etc.), to enable controlled release of active segments, when desired in relation to a protocol, from the body 110. In variations, activatable cleavage can be achieved with linkers configured to be cleave in response to one or more of: a thermal cleavage mechanism, a pH shift, a photocleaving mechanism, an enzymatic cleaving mechanism, or another suitable cleaving mechanism.

Furthermore, molecules of the first subset of molecules 120 and/or the second subset of molecules 130 can be confined during processing by restricting diffusion in an undesired manner. For instance, units of the composition can be confined within a suitable structure and/or using a confinement medium (e.g., hydrogel medium, viscous medium, etc.), in order to prevent diffusion of released molecules and/or functionalized particles away from a desired position.

In still other variations, molecules of the first subset of molecules 120 and the second subset of molecules can be otherwise configured and/or include additional functional segments.

2.4 Configurational Example for Determining Nearest Neighboring Particles

Figure 4:
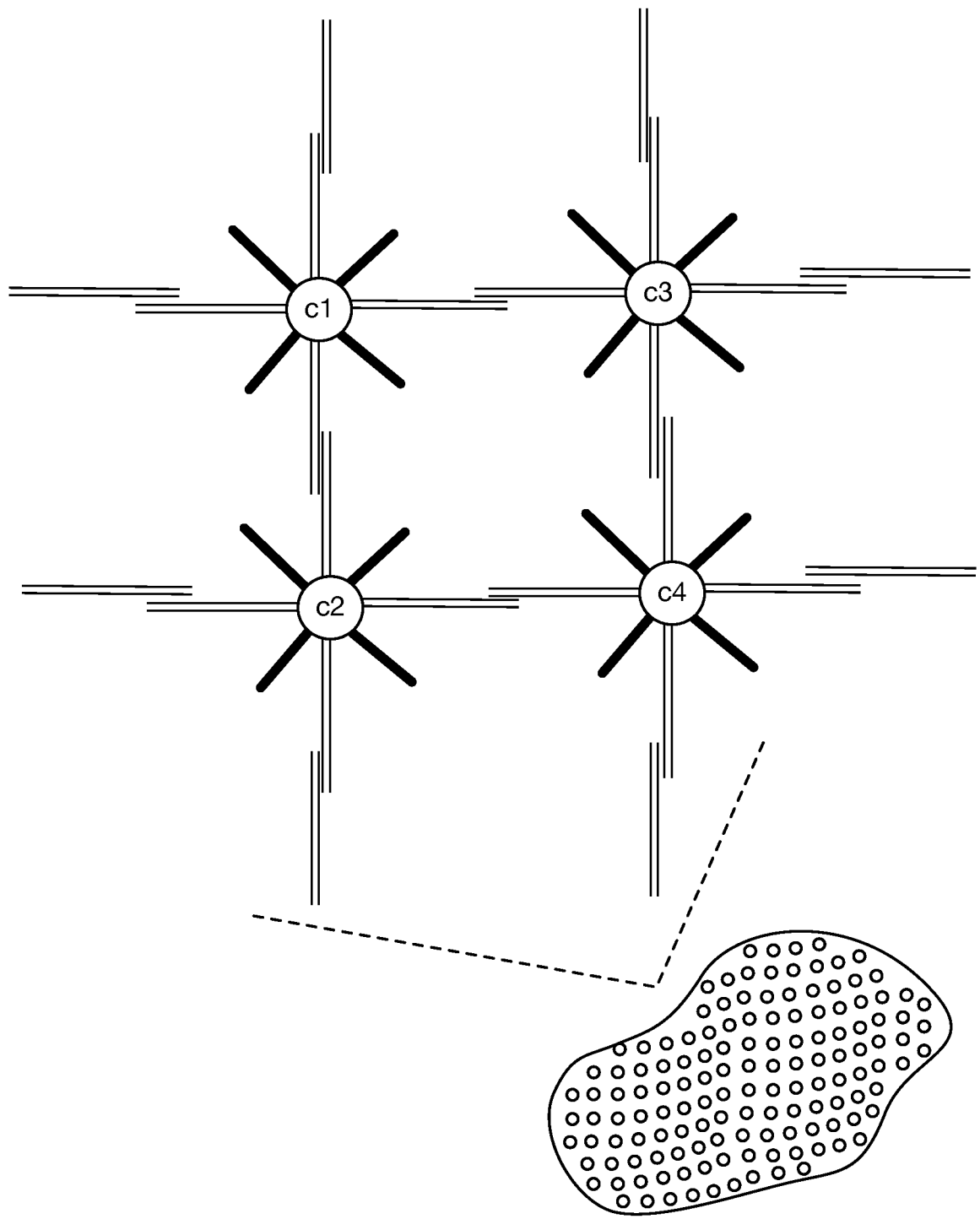
FIG. 4 depicts an embodiment of an application of use for the composition.

FIG. 4 depicts a configurational example of a 2D network of particles of the composition(s) described above. In the example, each particle is positioned at a node (i.e., C1, C2, C3, C4, ..., Cn), and each particle has functionalized molecules having particle identification segments (Lp), as described above, where the Lp particle identification segments have regions to be copied during sample processing, in order to allow identification of nearest neighbors.

In variations of example, for a particle having a characteristic dimension (D) and surface area (A), with a density of functional sites (C) defined in terms of surface area, a particle would have a number of functional sites (F)=AC. To enable nearest neighbor interactions, a critical distance (d) between particles would need to be established, where d is equal to 2× the length of the linker region described above. Thus, to map targets in a 2D space [S] that could be approximated as a rectangle with a characteristic length (l) and characteristic width (w), at least l/d×w/d particles would be needed within [S], and the number of functional sites for target capture would be equal to F(l/d)(w/d), in order to map targets in [S]. Similarly, for a 3D volume having a characteristic height (h), F(l/d)(w/d)(h/d) functional sites for target capture would be provided (however, other volume approximations can be implemented in other variations). Additionally or alternatively, the method can be adapted to other functions of distributions of particles within a 2D space or 3D volume that are not rectangular or rectangular prismatic.

Thus, for a particle having a characteristic dimension of 100 nm, the surface area (e.g., $4\pi r^2$) is approximately $3\times10^6$ $A^2$, and assuming that there are $10^{-4}$ functional sites/$A^2$, each particle would have ~300 functional sites. Then, to enable nearest neighbor interactions, a critical distance (d) between particles would need to be established, where d is equal to 2× the length of the linker region described above. For a PEG linker having a characteristic length of 500 Å, d=1 um. Thus, in a cell having a characteristic dimension of 5 um, ~5 particles of the example composition could be placed across each axis of a plane defined by the cell (i.e., 25 particles/plane), thereby allowing 5*25=125 particles to be distributed across the cell. With an estimated 300 functional sites per particle described above, such a configuration would provide ~625×300=180,000 functional sites for mRNA capture (or capture of another suitable target).

Such a particle configuration could be used in the context of single cell analyses, where a distribution of particles could be "infused" into the cells for mapping of sub-cellular scale targets. Additionally or alternatively, variations of such a distribution of particles could be used to tissue-scale analyses, organ-scale analyses, organism-scale analyses, and/or other suitable analyses.

While a 2D example is described, the configurational example can be expanded to 3D dimensional non-random networks and/or randomly organized networks. For instance, the 2D example of a tissue slice can be expanded to applications involving tissue blocks (e.g., amorphous tissue blocks in 3D space, tissue blocks of other form factors, 3D scaffolds seeded with biological material, etc.), Additionally or alternatively, applications of the example can be applied to a suspension of particles, cells, droplets or other material immobilized in a 3D medium.

3. METHOD

Figure 5:
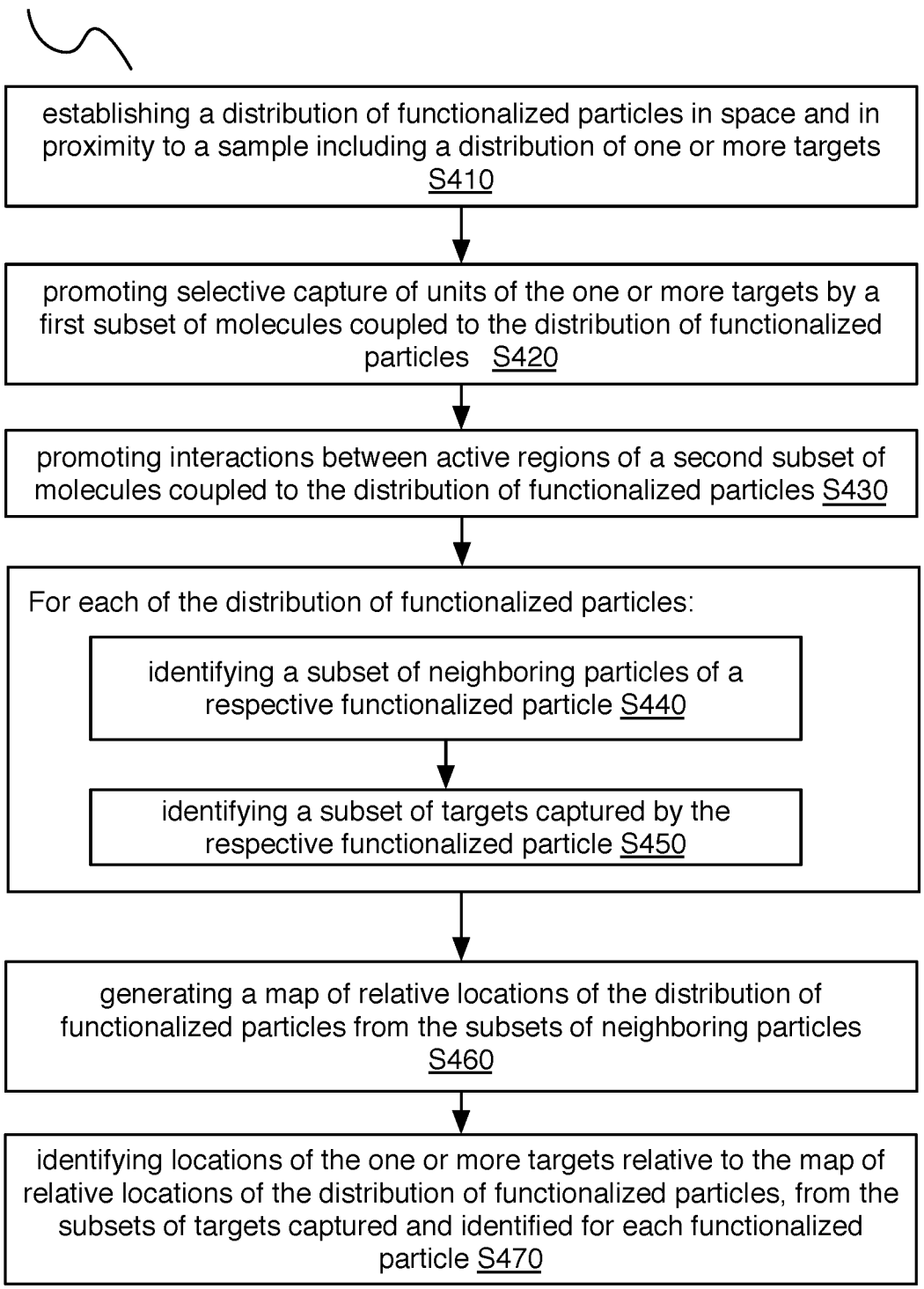
FIG. 5 depicts an embodiment of a method for mapping locations of targets in multidimensional space.

As shown in FIG. 5, a method 400 for mapping locations of targets (e.g., single molecules, other targets) in multi-dimensional space (e.g., one-dimensional space, two-dimensional space, 3-dimensional space) can include: establishing a distribution of functionalized particles in space and in proximity to a sample including a distribution of one or more targets S410; promoting selective capture of units of the one or more targets by a first subset of molecules coupled to the distribution of functionalized particles S420; promoting interactions between active regions of a second subset of molecules coupled to the distribution of functionalized particles S430; for each of the distribution of functionalized particles: identifying a subset of neighboring particles S440 of a respective functionalized particle; and identifying a subset of targets captured by the respective functionalized particle S450; generating a map (e.g., spatial map) of relative locations of the distribution of functionalized particles from the subsets of neighboring particles S460; and identifying locations of the one or more targets relative to the map of relative locations of the distribution of functionalized particles, from the subsets of targets captured and identified for each functionalized particle S470.

Embodiments of the method 400 function to facilitate capture of target biological material from a sample, with mapping of distributions of target biological material in space (e.g., two dimensional space, three dimensional space). Embodiments of the method 400 also function to provide mechanisms for efficient capture and labeling of target material (e.g., DNA, RNA, miRNA, proteins, small molecules, single analytes, multianalytes, etc.) in order to enable analyses for mapping distributions of target material in multidimensions (e.g., 2D, 3D), where mapping can be performed in relation to whole tissue structures, tissue pieces (e.g., as in histology, in relation to biopsied tissues, in relation to seeded natural scaffolds, etc.), organs, whole organisms, cell suspensions, droplets (e.g., of an emulsion), single cells, organelles, within organelles, viruses, microorganisms, and other natural structures. Mapping can additionally or alternatively be performed in relation to non-naturally occurring structures, such as microwells, microarrays, scaffolds, and other non-naturally occurring structures.

The method 400 can be enabled by embodiments, variations, and examples of the compositions described above, and/or other suitable systems and compositions.

3.1 Method—Distribution of Functionalized Particles

Block S410 recites: establishing a distribution of functionalized particles in space and in proximity to a sample including a distribution of one or more targets. Block S410 functions to distribute functionalized particles in space, and in a manner that allows interactions between neighboring functionalized particles, along with selective capture of targets of the sample.

In variations, Block S410 can include distributing functionalized particles in an ordered manner (e.g., 1D array, 2D array, 3D array, etc.). In such variations, distributing functionalized particles in an ordered manner can include implementing one or more structures for retention of the functionalized particles in position, where, in examples, structures can include substrates (e.g., substrates patterned with the distribution of functionalized particles), microwells, microarrays (e.g., with nucleic acids capturing particles), scaffolds, or other 3D structures. Additionally or alternatively, Block S410 can include retaining functionalized particles in position by use of forces (e.g., magnetic forces for functionalized magnetic particles, electrical forces/charged surfaces, gravitational forces, forces applied using acoustic or other vibration, centrifugal forces, buoyancy forces, chemical binding, etc.). In these variations, the method 400 can include releasing retained functionalized particles from a support structure by one or more of: application of magnetic forces of reverse polarity or removal of a magnetic field (e.g., for functionalized magnetic particles), application of reverse polarity charge or other removal of electrical forces, removal of gravitational forces, removal of forces applied using acoustic or other vibration, application of a detergent to remove chemical bonds, and/or other suitable mechanisms. As such, retention and release can be performed in a reversible or non-reversible manner.

Alternatively, Block S410 can include distributing functionalized particles in a random manner (e.g., in a randomly-dispersed manner, in solution, within an emulsion, within droplets of an emulsion, etc.).

In relation to establishing the distribution of functionalized particles, Block S410 can include positioning the distribution of functionalized particles adjacent to (e.g., in contact with) a sample (e.g., cell sample, tissue, sample, etc.). Additionally or alternatively, Block S410 can include infusing functionalized particles into a sample (e.g., into a cell, into a tissue, into an organ, etc.). Examples of infusion can include one or more of: injection, electroporation, use of vectors (e.g., viral vectors), and other infusion methods. Additionally or alternatively, Block S410 can include dispersing the functionalized particles amongst portions of the sample (e.g., in relation to a cell suspension, in relation to a disperse tissue, in relation to other samples with disperse components). Additionally or alternatively, Block S410 can include coupling functionalized particles to a surface of a sample/specimen (e.g., by chemical binding, by magnetic binding, by other binding. In a related application, Block S410 can implement physical or other forces to define structures (e.g., close packed structures) for distributions of particles that interact with samples to enable mapping.

In variations wherein the functionalized particles are distributed in space in an ordered manner (e.g., as an array), the manner in which the functionalized particles is distributed can be used to apply boundary conditions/constraints to mapping algorithms described in more detail below. Additionally or alternatively, in variations involving random distributions of functionalized particles, mapping algorithms described in more detail below can apply assumptions associated with random dispersal of particles.

3.2 Method—Target Capture by Particles

Block S420 recites: promoting selective capture of units of the one or more targets by a first subset of molecules coupled to the distribution of functionalized particles. Block S420 functions to implement capture probes of a subset of molecules coupled to core bodies of the functionalized particles, as described above, to capture targets of the sample. Promoting selective capture can include processing the sample with the set of functionalized particles in a suitable environment (e.g., with respect to solution, temperature, pH, concentration of components, flow, washing, reagents, etc.). Additionally or alternatively, promoting selective capture can include other suitable processing steps (e.g., lysis of sample components, washing of undesired sample components, etc.).

In one variation, described in relation to FIG. 2A above, Block S420 can include capturing target mRNAs of the sample (e.g., using capture probes with dT, dTVN for capturing polyA mRNAs), followed by reverse transcription to append the capture probes with cDNA. In alternative variations, block S420 can include promoting selective capture of one or more of: DNA, other RNA (e.g., miRNA), proteins (e.g., antibodies, using TotalSeq™ molecules), small molecules, single analytes, multianalytes, etc.), and/or other target material using suitable capture probes. As such, for nucleic acid targets, capture probes of a first subset of molecules coupled to the functionalized particles can include complementary molecules to the nucleic acid targets. For protein targets or small molecule targets, such targets can be tagged with an oligonucleotide having a sequence complementary to that of the capture probes.

3.3 Method—Nearest Neighbor Interactions

Block S430 recites: promoting interactions between active regions of a second subset of molecules coupled to the distribution of functionalized particles. Block S430 functions to enable interactions between neighboring functionalized particles, thereby allowing neighboring particles to interact in a manner that allows mapping of particle distributions, as described in more detail below. Promoting interactions can include processing the sample with the set of functionalized particles in a suitable environment (e.g., with respect to solution, temperature, pH, concentration of components, flow, washing, reagents, etc.).

Block S430 can include implementing linker portions of a second subset of molecules coupled to core bodies of the functionalized particles, as described above, where the linker portions extend molecules into space for nearest neighbor interactions. In relation to distributions of particles, the minimum distances between adjacent particles can be defined in relation to 2× the length of the linker, such that active segments of functionalized particles are close enough to interact with each other.

In variations, examples of which are shown in FIGS. 3A-3C, interactions associated with Block S430 can include hybridization of complementary sequences followed by polymerase extension, by way of implementing sticky ends followed by ligation, by way of implementing blunt end ligation, or by another suitable mechanism.

An example of interaction using hybridization and polymerase extension is shown in FIG. 3A, as described above. An example of interaction using sticky ends followed by ligation is shown in FIG. 3B, as described above. An example of interaction using blunt ends followed by ligation is shown in FIG. 3C, as described above.

Blocks S420 and S430 can occur contemporaneously (e.g., simultaneously, near in time to each other, in parallel). Additionally or alternatively, Blocks S420 and S430 can occur sequentially.

3.4 Method—Neighbor Identification and Target Detection

For each of the distribution of functionalized particles, embodiments of the method 400 include: Block S440, which recites: identifying connectivity of a subset of neighboring particles S440 of a respective functionalized particle; and Block S450, which recites: identifying a subset of targets captured by the respective functionalized particle. Blocks S440 and S450 function to identify: 1) configurations of neighboring functionalized particles, post interactions between active segments of the neighboring functionalized particles, and 2) targets captured by the functionalized particles. Thus, information extracted from Blocks S440 and S450 can be used to map distributions/locations of targets of the sample in space during subsequent portions of the method.

Block S440 can include sequencing of connections (e.g., active regions of functionalized particles that have interacted with each other) between interacting nearest neighbors (e.g., post-amplification of connections), as described above, where particle identification segments can be used to understand which functionalized particles interacted with each other. In one variation, high throughput sequencing can be used for readout of the connections of neighboring particles to extract information for mapping target distributions. Additionally or alternatively, other sequencing approaches can be used to readout connections between interacting nearest neighbors.

Similarly, Block S450 can include sequencing of target molecules captured by capture probes of the set of functionalized particles (e.g., post reverse transcription and amplification of synthesized cDNA, for mRNA applications described above). In one variation, high throughput sequencing can be used for readout of the target molecules captured. Additionally or alternatively, other sequencing approaches can be used for readout of the target molecules captured.

3.5 Method—Mapping of Particles and Distributions of Targets

Block S460 recites: generating a map of relative locations of the distribution of functionalized particles from connectivities of the subsets of neighboring particles, which functions to process information derived from Block S440 to understand which particles were neighboring each other during interactions with targets of the sample. Block S460 can be implemented by one or more computing systems with one or more processors for processing sequencing data from Block S440, in order to generate the map of relative locations of the distribution of functionalized particles.

Block S460 can include processing the sequencing data for connections between neighboring particles (as described in relation to Block S440), in combination with sequencing of particle identification segments, to identify subsets of functionalized particles that were neighboring each particle. As such, Block S460 can implement a connectivity algorithm (e.g., using graph theory), mapping algorithms, network algorithms, and/or other suitable algorithms based on the particle identification segments and connections sequenced.

Algorithms used in Block S460 can be used in coordination with location algorithms, in order to allow mapping of positions of particles at specific locations of a 1D, 2D, or 3D structure. As such, in variations of the method 400 involving ordered or otherwise structured configurations of functionalized particles (e.g., using arrays, using forces, using close packing, etc.), location algorithms can implement structural definitions as constraints, in order to map positions of functionalized particles within a space that is pre-defined or otherwise known.

Additionally or alternatively, Block S460 can implement algorithms that account for distances between neighboring particles (e.g., using linker portion lengths, etc.), thereby allowing mapping of functionalized particles in less structured or unstructured configurations (e.g., involving functionalized particles randomly dispersed in solution, involving functionalized particles infused into a sample, etc.).

Figure 6:
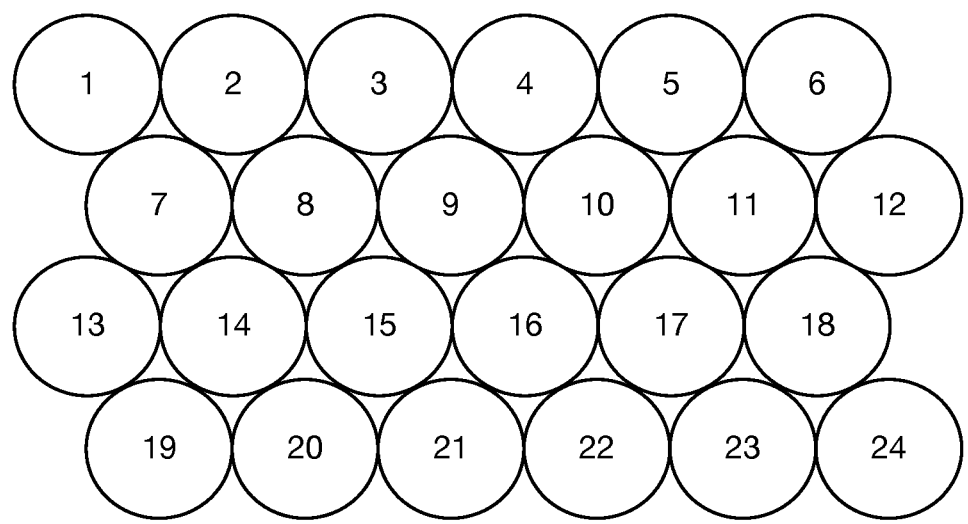
FIG. 6 depicts an example configuration of particles used for mapping locations of targets in multidimensional space.

In an example, as shown in FIG. 6, Block S460 can process sequencing data from Block S440, to determine connections between functionalized particles. Using particle 9 (shown in FIG. 6) as an example, processing of sequencing data from Block S440 would return particles 3, 4, 10, 16, 15, and 8 as neighboring particles. Similarly, using particle 10 (shown in FIG. 6) as an example, processing of sequencing data from Block S440 would return particles 4, 5, 11, 17, 16, and 9 as neighboring particles. Implementing boundary constraints based upon pre-defined close-packing of particles, would further be implemented in Block 460 to map positions of particles in space, based upon the known close-packing configuration.

Block S470 recites: identifying locations of the one or more targets relative to the map of relative locations of the distribution of functionalized particles, from the subsets of targets captured and identified for each functionalized particle. Block S470 functions to process information derived from Block S450 to understand which targets were captured by each capture probe of respective functionalized particles during sample processing in preceding steps. Block S470 can be implemented by one or more computing systems with one or more processors for processing sequencing data from Block S450, in order to locate captured targets relative to particles of the distribution of functionalized particles mapped out in Block S460.

Block S470 can include processing the sequencing data for targets captured and/or capture probes (as described in relation to Block S450), in combination with sequencing of particle identification segments, to identify a subsets of functionalized particles that were neighboring each particle. As such, Block S460 can process sequencing data for captured targets from Block S450, and with the particle identification segments corresponding to the captured targets, label each functionalized particle with its respective captured targets. As such, returned outputs of Block S470 can include mappings of locations of targets of a sample in space.

In relation to the example shown in FIG. 6, outputs of Block S470 can be used to map captured targets (e.g., mRNA species of a sample) in space (e.g., 1D space, 2D space, 3D space, etc.), based upon the mapping of functionalized particles generated in Block S460. For instance, outputs of Block S470 can reveal that particles 9, 10, 17, and 23 capture a first target (e.g., mRNA species 1), thereby allowing mapping of the first target in space, by integrating information derived from the mapping of Block S460. Similarly, outputs of Block S470 can reveal that particles 1, 2, 3, 8, 14, and 19 capture a second target (e.g., mRNA species 2), thereby allowing mapping of the second target in space, by integrating information derived from the mapping of Block S460. Variations of the example can be implemented in another suitable manner.

Downstream applications of outputs of Block S470 can thus be used to understand distributions of targets of a sample and/or changes in distributions of targets over time, with repeat implementation of the method 400.

The method 400 can, however, include other suitable steps and/or enable other downstream applications.

5. CONCLUSION

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A composition comprising a plurality of bodies, wherein a body of said plurality of bodies comprises:
a set of nucleic acid molecules coupled to the body, the set of nucleic acid molecules comprising a first subset of nucleic acid molecules and a second subset of nucleic acid molecules,
wherein a first nucleic acid molecule of the first subset of nucleic acid molecules comprises:
a capture probe comprising a sequence complementary to a target analyte; and
wherein a second nucleic acid molecule of the second subset of molecules comprises:
a linker region configured to extend the second nucleic acid molecule of the second subset of nucleic acid molecules into space beyond a first terminal end of the first nucleic acid molecule of the first subset of nucleic acid molecules,
an anchor segment,
a body identification segment, and
an active segment positioned at a second terminal end of the second molecule, wherein the active segment is coupled to at least a portion of an additional active segment of an additional nucleic acid molecule of an additional body of the plurality of bodies.

2. The composition of claim 1, wherein said body of said plurality of bodies comprises a magnetic material.

3. The composition of claim 1, wherein the capture probe comprises a sequence complementary to a target messenger ribonucleic acid molecule (mRNA) molecule.

4. The composition of claim 1, wherein the linker region comprises a non-nucleic acid polymer.

5. The composition of claim 1, wherein the active segment comprises a sequence hybridized with a sequence of the additional active segment.

6. The composition of claim 5, wherein the second nucleic acid molecule comprises a first sticky end comprising the active segment and wherein the additional nucleic acid molecule comprises a second sticky end comprising the additional active segment.

7. The composition of claim 1, wherein the second nucleic acid molecule comprises a first blunt end comprising the active segment, and wherein the additional nucleic acid molecule comprises a second blunt end comprising the additional active segment, and wherein the first blunt end and the second blunt end are ligated together.

8. A substrate comprising the composition of claim 1, wherein bodies of the plurality of bodies are distributed across the substrate.

\* \* \* \* \*